United States Patent [19]

Shasha et al.

[11] Patent Number: 5,720,968
[45] Date of Patent: Feb. 24, 1998

[54] DEVICE FOR CONTROLLING PESTS

[75] Inventors: Baruch S. Shasha; Michael R. McGuire, both of Peoria, Ill.; Xing Ping Hu, Amherst; Ronald J. Prokopy, Conway, both of Mass.

[73] Assignee: The United States of America as represented by the Secretary of the Agriculture, Washington, D.C.

[21] Appl. No.: 701,088

[22] Filed: Aug. 21, 1996

[51] Int. Cl.⁶ .................................................. A01N 25/10
[52] U.S. Cl. .................. 424/410; 424/406; 424/408; 424/409; 424/418
[58] Field of Search ........................... 424/405, 408, 424/409, 410, 418–420, 84

[56] References Cited

U.S. PATENT DOCUMENTS

| | | | |
|---|---|---|---|
| 1,618,702 | 2/1927 | Forsell | 424/410 |
| 4,411,754 | 10/1983 | Kaetsu et al. | 424/487 |
| 5,484,587 | 1/1996 | Branly et al. | 424/84 |
| 5,516,520 | 5/1996 | Yang et al. | 424/408 |
| 5,571,522 | 11/1996 | Munson et al. | 424/410 |

FOREIGN PATENT DOCUMENTS 643722 7/1991 Australia.

OTHER PUBLICATIONS

J.J. Duan and R.J. Prokopy, "Toward developing pesticide-treated spheres for controlling apple maggot flies, *Rhagoletis pomonella* (Walsh) (Dipt., Tephritidae)", U. of Massachusetts, Dept. of Entomology, Amherst, USA (1993), pp. 176–184.

Jian J. Duan and Ronald J. Prokopy, "Control of Apple Maggot Flies (Diptera: Tephritidae) with Pesticide-Treated Red Spheres" Horticultural Entomology, (1995) pp. 700–707.

Jian J. Duan and Ronald J. Prokopy, "Development of Pesticide-Treated Spheres for Controlling Apple Maggot Flies (Diptera: Tephritidae): Pesticides and Residue-Extending Agents", Horticultural Entomology, 1995, pp. 117–126.

R.J. Prokopy, J.J. Duan and X.P. Hu, "Toxicant-Treated Red Spheres for Controlling Apple Maggot Flies", New England Fruit Meltings, vol. 101 (1995).

Alan H. Reynolds et al., "Apple Maggot Fly (Diptera: Tephritidae) Response to Perforated Red Spheres",U. of Massachusetts, Dept. of Entomology, Amherst, USA (in press) Jun. 1996.

J.J. Duan and R.J. Prokopy, "Toward developing pesticide-treated spheres for controlling apple maggot flies, *Rhagoletis pomonella* (Walsh) (Dipt., Tephritidae)", *J. Appl. Ent.* 115, pp. 176–184 (1993).

Jian J. Duan and Ronald J. Prokopy, "Control of Apple Maggot Flies (Diptera: Tephritidae) with Pesticide-Treated Red Spheres" *J. Econ. Entomol.* 88(3): pp. 700–707 (1995).

Jian J. Duan and Ronald J. Prokopy, "Development of Pesticide-Treated Spheres for Controlling Apple Maggot Flies (Diptera: Tephritidae): Pesticides and Residue-Extending Agents", *J. Econ. Entomol.* 88(1): pp. 117–126 (1995).

R.J. Prokopy, J.J. Duan and X.P. Hu, "Toxicant-Treated Red Spheres for Controlling Apple Maggot Flies", *New England Fruit Mtngs*, vol. 101 pp. 71–77 (1994).

Alan H. Reynolds et al., "Apple Maggot Fly (Diptera: Tephritidae) Response to Perforated Red Spheres", *Florida Entomotogist*, vol. 70, No. (2), Jun., 1996.

Xingping Hu, John Clark, and Ronald Prokopy, "Progress in 1995 Toward Development of Toxicant-treated Spheres for Controlling Apple Maggot Flies", *Fruit Notes*, vol. 61, No. 2, Spring Issue, 1996.

*Primary Examiner*—Neil S. Levy
*Attorney, Agent, or Firm*—Arnold, White & Durkee

[57] ABSTRACT

The present invention is a device for delivering pesticide to pests, comprising (a) an outer layer comprising a porous water-insoluble polymeric; (b) an inner layer in contact with the outer layer, the inner layer comprising a water-soluble feeding stimulant and a carbohydrate which is at least partially gelatinized; and (c) a toxicant which is present on or in the outer layer, the inner layer, or both. The types of pests for which the device may be used to deliver pesticide are any pests which are able to be controlled by the toxicants used in the device and that can be attracted to an object to feed and/or lay eggs, such as the apple maggot fly, the Mediterranean fruit fly, the house fly, the oriental fruit fly, the blueberry fruit fly, the olive fruit fly, the melon fruit fly, and the Mexican fruit fly as well as other flies, beetles, wasps, moths, cockroaches, and any other insect that can be lured to a device for feeding or egg laying.

The porous water-insoluble polymeric materials are pits, shellacs, linseed oil and other water soluble or water suspendible material that becomes insoluble upon drying. Examples of water-soluble feeding stimulants are sugary products chosen from the group consisting of sucrose, glucose, fructose, molasses, maltodextrins, and corn syrup as well as corn flour, gluten or other sugary or proteinaceous and lipid materials for insects other than flies. Examples of carbohydrates are corn flour, cornstarch, wheat starch, and potato starch. Toxicants which may be used are dimethoate, phyloxine B, avermectin, azinphosmethyl, diazinon, permethrin, Imidacloprid, Malathion, Methomyl, or other insecticides available in sufficient quantity to kill insects upon feeding or alighting on the sphere. A high boiling liquid such as glycerin may optionally be added to the carbohydrate/first layer of the device to prevent cracking.

25 Claims, No Drawings

DEVICE FOR CONTROLLING PESTS

BACKGROUND OF THE INVENTION

The invention relates to a device and method for controlling insect pests on fruit, in particular to controlling fruit flies.

One example oaf an insect pest which attacks fruit is the apple maggot. From July until harvest, the apple maggot attacks apple fruit in New England and many other regions of eastern and central North America. Annually, a high percentage of fruit on unmanaged apple trees in Massachusetts is injured by apple maggot, while commercial apple growers in Massachusetts control the amount of injury by applying about 3 sprays. Except in the case of Golden Delicious and a few other cultivars that ripen very late, three pesticide applications per year usually provide excellent and comparatively inexpensive maggot control.

Alternatives to the use of pesticides for maggot control are of interest for a number of reasons. Pesticides such as Guthion™, Imidan™, and other pesticides commonly used to control apple maggot are known to be toxic to several sorts of beneficial insects in orchards as well as toxic to the apple maggots themselves. There is growing evidence that withholding all insecticide use during summer will permit the buildup of these beneficial insects; examples of these insects are wasp parasitoids of leafminers, fly and ladybug predators of aphids, yellow mite predators of spider mites, and spider predators of leafhoppers.

Problematic pests such as leafminers, aphids, mites, and leafhoppers have developed resistance to Guthion, Imidan and most other pesticides used to control apple maggot. In consequence, growers have had to resort to using additional types of pesticides specifically targeted against these resistant pests. Most of these additional types are not only very expensive but, because of the rather narrow market niche, are also subject to withdrawal by companies who cannot afford to re-register compounds directed only at one or two pests. Moreover, foliar pest resistance to new types of pesticide is just as much of a reality or threat as was resistance to Guthion and Imidan. Avoiding the use of pesticides and allowing the buildup of natural enemies will reduce pesticide pressure that leads to development of pesticide resistance.

Contamination of the environment by pesticides is of great concern. Some orchard spray unavoidably drifts into areas bordering orchards. Using a non-pesticidal method of maggot control could alleviate all need to apply insecticide after early June and do much to allay the problems associated with drift.

The potential alternatives to pesticides for maggot control include biological agents, improved management of orchards and the neighborhoods which surround them, choosing more resistant cultivars of apples, and controlling the behavior of the pests. Biological control brought about by the use of agents such as predators, parasitoids and pathogens often provides very effective suppression of kinds of pests that can be tolerated in small or moderate numbers without causing economic injury. It is extremely unlikely, however, that augmentation of existing natural enemies or importation of beneficials from abroad would reduce maggot populations on unmanaged trees to a level so low that immigrating flies would cease to be a threat to commercial orchards.

Control of pests can also be done by removing all unmanaged apple and hawthorn trees within a prescribed distance of a commercial orchard and thereby eliminating sources of immigrant maggot flies. The practice of removing all unmanaged apple and pear trees within 100 yards of the orchard perimeter has worked well in controlling codling moth in Massachusetts. But as female apple maggot flies are known to move much greater distances (even as much as a mile) than female codling moths, removing all wild maggot fly hosts within a mile of an orchard is not feasible, operationally or sociologically.

Most current cultivars of apples that are of high customer appeal are at least moderately if not highly susceptible to maggot fly egg laying and early larval development, obviating an approach based solely on cultivar resistance. Indeed, there is little reason to be hopeful that host fruit tolerance or resistance will play an important role in maggot fly management in the near future because selection of apple cultivars for planting is based largely on appeal to consumers rather than on appeal to pests.

Behavioral control offers the most promise as an alternative approach to maggot fly management in commercial orchards. Maggot flies have proven highly responsive to synthetic fruit and food odor stimuli and to synthetic fruit visual stimuli, affording the possibility of luring and killing the flies before they can cause injury.

Present traps for fruit insect behavioral control employ attractive odor and visual stimuli to lure insects to the trap. One of three methods is used to kill insects arriving at the trap: (1) the exterior of trap is coated with polymeric sticky material to entangle arriving insects, which cannot escape, (2) the exterior of a non-sticky trap is perforated with holes, through which arriving insects enter in response to an attractant in the trap interior; the insects are killed upon exposure to a small amount of insecticide in the trap interior, or (3) the exterior of a non-sticky trap is impregnated with a massive dose of highly toxic pesticide which kills arriving insects by direct contact within a few seconds.

Each of these traps has a major shortcoming. (1) Applying sticky material to traps is a messy process; further, maintenance of such traps is laborious as they must be cleaned of captured insects and debris at least every two weeks to maintain their effectiveness. (2) Perforated traps entice only a minority (in some species none) of the insects which arrive at the trap to enter the holes on the surface. The majority of the insects fly away without entering the perforations. (3) The amount of highly toxic pesticide which must be present on a trap to kill an arriving insect poses a danger to persons who touch the trap or breathe air in the vicinity of the trap.

The present invention provides a device which does not employ sticky material, does not rely on insects having to enter holes in the trap exterior, and does not employ large amounts of toxicant. It is much simpler and easier to handle than a sticky trap and is maintenance free.

SUMMARY OF THE INVENTION

The present invention is a device for delivering pesticide to pests, comprising (a) an outer layer comprising a porous water-insoluble polymeric material; (b) an inner layer in contact with the outer layer, the inner layer comprising a water-soluble feeding stimulant and a carbohydrate which is at least partially gelatinized; and (c) a toxicant which is present on or in the outer layer, the inner layer, or both. The toxicant may be present anywhere in the device, i.e., on the surface of either or both layers and/or incorporated into either or both layers. The types of pests for which the device may be used to deliver pesticide are any pests which are able to be controlled by the toxicants used in the device and that can be attracted to an object to feed and/or lay eggs, such as the apple maggot fly, the Mediterranean fruit fly, the house fly, the oriental fruit fly, the blueberry fruit fly, the olive fruit fly, the melon fruit fly, and the Mexican fruit fly as well as other flies, beetles, wasps, moths, cockroaches, and any other insect that can be lured to a device for feeding or egg laying.

The device of the present invention makes it possible to control release of water-soluble feeding stimulant which attracts pests to feed on the device and thereby ingest toxicants. The device also makes possible the prevention of cracking of the carbohydrate portion upon drying. Where cracking is a problem, a liquid which will evaporate slowly, e.g., a high boiling liquid such as glycerin or ethylene glycol, is added to the inner layer.

The porous water-insoluble polymeric materials are water soluble or water suspendible material that becomes insoluble upon drying such as paints, shellacs, linseed oil.

The water-soluble feeding stimulant is a sugary product chosen from the group consisting of sucrose, glucose, fructose, molasses, maltodextrins, and corn syrup. Examples of other possible feeding stimulants for insects other than flies are corn flour, gluten or other sugary or proteinaceous and lipid materials.

Examples of the carbohydrate which is at least partially gelatinized and may be fully gelatinized are corn flour, cornstarch, wheat starch, and potato starch.

Toxicants which may be used are dimethoate, phyloxine B, avermectin, azinphosmethyl, diazinon, permethrin, Imidacloprid, Malathion, Methomyl, or other insecticides available in sufficient quantity to kill insects upon feeding or alighting on the sphere. A high boiling liquid such as glycerin may optionally be added to the carbohydrate/first layer of the device.

DETAILED DESCRIPTION OF THE INVENTION

The device of the present invention, which employs only a very small amount of toxicant, causes arriving insects to feed immediately after contact with the trap exterior and in so doing causes ingestion of a lethal dose of toxicant along with the feeding stimulant. It kills a much higher proportion of individuals of most species of arriving insects than does a non-sticky trap with holes because it kills virtually all arriving individuals rather than just a minority and it is capable of doing so over a period of several months of exposure to outdoor conditions, even conditions of high rainfall. The inventive device employs far less toxicant than traps impregnated with insecticide. It has considerable commercial potential in that it can be mass produced, mailed, removed from packaging and employed by the user without any action required by the user other than proper positioning of the device. The device of the present invention may be hung in fruit trees to control fruit fly pests of tree fruit.

In general, the device of the present invention comprises an outer layer having a thickness of from about 1 to about 1,000 microns, an inner layer of from about 3 to about 30 cm diameter, a water-soluble feeding stimulant of about 10–90 wt. %, preferably 20–50 wt. %. The amount of toxicant present in the device is an amount which will be effective for the control of the target pest.

The device of the present invention may contain a core. Examples of materials which may be used as a core in the center of the device in contact with the inner layer are paper, cheese cloth, wood or any other solid material capable of being shaped and coated.

The shape, size, color and texture of the device can be manipulated to attract harmful insects. Insect attractants may also be added to the device, the toxicant can be on the surface of either or both layers and/or incorporated into either or both layers, and a core material occupying interior space may be present.

Examples of insect attractants are fruit volatiles such as butyl hexanoate, hexyl acetate, or ammonia-based compounds such as ammonium carbonate or pheromones or other attractants that are known in the art.

The device of the present invention may be shaped into any form and is preferably spherical or fruit-shaped or in a shape known to be attractive to specific insect species.

The present invention also encompasses a method of delivering pesticide to pests utilizing the inventive device.

EXAMPLES

Example 1

General Testing Procedure

Simulated Rainfall Test. Three replicates of each formulation of the device were hung in a chamber that delivered artificial rainfall as a spray at a rate of one inch (2.54 cm) per hour. The device received one hour of rainfall per day up to 7 successive days, with 23 hours of drying time between rainfall exposure events. Continuous movement of the nozzle, back and forth, allowed for an even dispersion of water over the device. Runoff from each device was collected by a container set beneath it and submitted to chemical analysis for amount of compound runoff. The physical appearance of the spherical devices immediately following a rainfall test and two days after treatment was recorded.

Apple Maggot Fly Bioassay. In all cases two spherically-shaped devices of each formulation were hung from the branches of a potted non-fruiting apple tree within a 3×3×3 m field cage (protected from rainfall by a tarpaulin) and allowed to dry for one day before bioassays were conducted. Thirty apple maggot fly adults (15 males, 15 females) were released individually onto each sphere and allowed to remain there up to ten minutes. The proportion of flies feeding more than 30 seconds was recorded. If the flies were tested on spheres bearing a toxicant, each group of 30 flies was kept in a 30×30×30 cm aluminum screen/Plexiglas cage, after exposure, for 24 hours (except for those indicated) to assess percent mortality. Each cage was supplied with water and food. Flies originated from pupae collected from nature, emerged in laboratory cages, and were 10–15 days old when tested. In general, 90 flies were tested for each formulated device.

Example 2

Preparation of Samples

Various comparative and inventive devices were prepared in a spherical shape using the basic formulations outlined in Table 1.

TABLE 1

| Formulation | Description |
|---|---|
| A | 80 g sucrose was dissolved in 80 mL water that contained 2 g sodium bicarbonate. The mixture was heated to 80° C. and then 120 g pregelatinized corn flour 961 (from Illinois Cereal Mills) and 0.25 g powdered charcoal was added. |
| B | The same mixture as Formulation A except that 20 mL of the water was substituted with 20 mL glycerin. |
| C | 80 g ungelatinized wheat flour was mixed with 40 g pregelatinized corn flour 961 and then mixed with 60 mL of a 33% isopropyl alcohol solution. 20 g sucrose and 20 g high fructose syrup were added to the mixture and then the entire combination was cooked in a microwave oven for 30 seconds. |
| D | 80 g sucrose was dissolved in 80 mL water that contained 2 g sodium bicarbonate. The mixture was heated to 80° C. and then 120 g pregelatinized corn flour 961 mixed with 0.25 g Congo red preheated to 50° C. was added |
| E | 80 g sucrose was dissolved in a mixture containing 75 mL water and 15 mL glycerin. 80 g pregelatinized corn flour 961 was mixed with 0.25 g Congo red and heated to 50° C.. This mixture was then added to the previous mixture to form a dough like product. |
| F | 80 g sucrose was dissolved in a mixture containing 45 mL water and 20 g glycerin and then heated in the microwave for 60 sec. 60 g pregelatinized corn flour 961, 40 g wheat flour and 0.5 g charcoal were added to form a dough. |
| G | 2.7 mL dimethoate was dispersed with a mixture comprised of 100 g pregelatinized corn flour 961, 20 g wheat flour and 0.5 g charcoal using a mortar and pestle. A mixture containing 80 g high fructose syrup, 35 g water, and 30 g glycerine was heated for 55 sec in a microwave oven and then added to the flour mixture to form a dough. |
| H | 60 g sucrose was dissolved in 40 mL water and then 55 g high fructose syrup and 20 g glycerin were added. This was mixed with a combination containing 50 g pregelatinized corn flour 961 and 50 g wheat flour. The mixture was then heated in a microwave oven for 35 seconds, stirred and heated another 35 sec. The dough was used to prepare the device after cooling at room temperature for 2 min. |

Specific comparative samples 1–4, 13 and 14, and inventive samples 5–12 and 15–21 using these formulations were prepared as in Table 2. All samples were prepared by forming the dough of the formulation to form a sphere. The dough was shaped around a core material in samples containing cores.

TABLE 2

| Sample # | Formulation | Core | Coating |
|---|---|---|---|
| 1 (Comp) | A | none | none |
| 2 (Comp) | B | none | none |
| 3 (Comp) | C | none | none |
| 4 (Comp) | D | none | none |
| 5 | A | none | Mixture of phyloxine B: flat red paint in a ratio of 0.1:99.9 or a ratio of 1:99* |
| 6 | A | none | Mixture of phyloxine B: flat red paint in a ratio 1:99* |
| 7 | A | none | Mixture of dimethoate:flat red latex paint of 0.5:99.5 |
| 8 | D | none | Mixture of dimethoate:red latex gloss paint of 0.5:99.5 |
| 9 | B | none | Mixture of dimethoate:red semi-gloss latex paint of 0.5:99.5 |
| 10 | E | 9 g paper towels | Mixture of dimethoate:gloss black paint in a ratio of 0.5:99.5 |
| 11 | D | none | Mixture of dimethoate and linseed oil in a ratio of 0.5:99.5 |
| 12 | D | none | Mixture of dimethoate and shellac in a ratio of 0.5:99.5 |
| 13 (Comp) | F | none | none |
| 14 (Comp) | G | 5 g tissue | none |
| 15 | G | 5 g tissue | Mixture of 0.5% technical grade dimethoate in red gloss paint |
| 16 | G | 5 g tissue | mixture of 0.5% technical grade dimethoate in black gloss paint |
| 17 | E | 9 g paper towels | 0.5% avermectin in red gloss latex paint |
| 18 | E | 9 g paper towels | 1% azinphosmethyl in red gloss latex paint |
| 19 | E | 9 g paper towels | 2% diazinon in red gloss latex paint |
| 20 | E | 9 g paper towels | 3% permethrin in red gloss latex paint |

TABLE 2-continued

| Sample # | Formulation | Core | Coating |
|---|---|---|---|
| 21 | H | 5 g tissue | 6 g gloss enamel bright yellow paint containing dimethoate (0.06 mL of a 50% active ingredient formulation) |

*Phyloxine B is an experimental insecticide.
(Comp) = Comparative sample

Comparative samples 1–4, 13 and 14 were prepared without a coating on the outer surface of the spherical device. The remaining inventive samples differed from each other in the type of coating on the sphere and on whether they contained an inner core material.

Example 3

Simulated Rainfall Test of Uncoated Comparative Samples 1–4

As discussed above, comparative samples 1–4 were prepared without a coating on the outer surface of the sphere. Upon drying, obvious cracks were visible on the surface of these samples. These samples were subjected to the Simulated Rainfall Test. After exposure to artificial rainfall, the cracks in the samples enlarged and became more numerous. As cracking on the surface of the sphere is known to render it unacceptable to the fly, the Apple Maggot Fly Bioassay procedure was not performed.

Example 4

Simulated Rainfall Test on Coated Inventive Samples 5–12

Inventive samples 5–12 were subjected to the Simulated Rainfall Test and the Apple Maggot Fly Bioassay. The results appear in Table 3.

TABLE 3

| | % Apple Maggot Fly Mortality after Differing Levels of Rainfall | | | | |
|---|---|---|---|---|---|
| Sample | No Rain | 1 in. (2.54 cm) | 2 in. (5.08 cm) | 3 in. (7.62 cm) | Sphere Surface |
| 5 | 0 | 0 | 0 | 0 | intact |
| 6 | 45 | 0 | 0 | 0 | intact |
| 7 | 97 | 92 | 83 | 72 | intact |
| 8 | 97 | 93 | 84 | 74 | intact |
| 9 | 98 | 93 | 84 | 75 | intact |
| 10 | 98 | 94 | 86 | 76 | intact |
| 11 | 97 | 91 | 75 | 65 | intact |
| 12 | 96 | 93 | 84 | 72 | intact |

Inventive samples 5–12 demonstrate that coating the spheres with a polymeric material such as paint, shellac, or linseed oil prevents the spheres from cracking and allows the sugar to diffuse to the surface, thus extending the effective life of the sphere.

Example 5

Simulated Rainfall Test On Comparative Samples 13–14 and on Inventive Samples 15–16

Comparative samples 13 and 14 and inventive samples 15 and 16 were subjected to the Simulated Rainfall Test. The percentage of sugar and dimethoate rinsed off each sample during the Simulated Rainfall Test was measured. The sugar was analyzed using a spectrophotometer (DU 50, Beckman) and a colorimetric process described by Dubois (1956) and the dimethoate was analyzed using a Hewlett Packard 5970 Gas Chromatograph equipped with a nitrogen/phosphorus detector. The results appear in Tables 4 and 5.

TABLE 4

Percentage of Sugar Rinsed from Samples during Simulated Rainfall Test

| | Amount of Rainfall | | | | | | |
|---|---|---|---|---|---|---|---|
| Sample | 1 in. (2.5 cm) | 2 in. (7 cm) | 3 in. (7.6 cm) | 4 in. (10 cm) | 5 in. (13 cm) | 6 in. (15 cm) | 7 in. (18 cm) |
| 13 | 3.0 | 5.2 | 8.2 | 11.0 | * | * | * |
| 14 | 3.5 | 6.7 | 11.2 | 15.7 | * | * | * |
| 15 | 1.4 | 3.0 | 5.0 | 6.3 | 7.4 | 8.3 | 9.4 |
| 16 | 1.2 | 2.5 | 4.3 | 6.0 | 7.0 | 8.0 | 9.0 |

*Spheres were too cracked to warrant further evaluation.

TABLE 5

Percentage of Dimethoate Rinsed from Samples using Simulated Rainfall

| | Amount of Rainfall | | | |
|---|---|---|---|---|
| Sample | 1 in. (2.54 cm) | 2 in. (7.08 cm) | 3 in. (7.62 cm) | 4 in. (10.16 cm) |
| 14 | 1.21 | 2.4 | 3.7 | 4.0 |
| 15 | 1.0 | 1.7 | 2.2 | 2.6 |
| 16 | 0.8 | 1.5 | 2.1 | 2.5 |

The above results show that coatings on the exterior of the sphere reduced leaching of dimethoate and sucrose.

Example 6

Natural Rainfall and Weathering of Comparative Sample 14 and Inventive Samples 15 and 16

Twelve samples of each of Samples 14–16 and a control were hung from branches of apple trees at the Horticultural Research Center of University of Massachusetts in early July. After 0, 1, 3, 5, 7 and 10 weeks, two spheres of each type were brought to the laboratory for bioassay. Natural rainfall during each period was recorded as measured by a rain gauge. The physical appearance of each sphere was recorded and the residual insecticidal activity was evaluated by the Apple Maggot Fly Bioassay. The results appear in Tables 6 and 7.

TABLE 6

| Sample | Apple Maggot Fly Mortality (%) | | | | |
|---|---|---|---|---|---|
| | 0 week | 1 week | 3 weeks | 5 weeks | 7 weeks |
| Control* | 98 | 43 | 22 | 0 | 0 |
| 14 | 98 | 80 | 56 | 24 | 0 |
| 15 | 98 | 91 | 86 | 72 | 68 |
| 16 | 97 | 94 | 87 | 73 | 70 |
| Natural rainfall, inches (cm) | 0 (0) | 0.2 (0.51) | 0.75 (1.9) | 3.45 (8.8) | 6.2 (15) |

*Wooden spheres coated with a mixture of 60% sucrose, 0.5% dimethoate and 39.5% red latex paint.

TABLE 7

| Sample | 0 week | 1 week | 3 weeks | 5 weeks | 7 weeks |
|---|---|---|---|---|---|
| Control | N/A | N/A | N/A | N/A | N/A |
| 14 | intact | intact | slight cracking | severe cracking | severe cracking |
| 15 | intact | intact | intact | intact | slight cracking |
| 16 | intact | intact | intact | intact | hairline cracking |

Note:
Control was not subject to cracking.

The results show that a coating of red or black paint will cause retention of pesticidal activity under natural environmental weather conditions while uncoated spheres lose activity after five weeks.

Example 8

Use with a Variety of Pesticides—Samples 17–20

Samples 17–20 were prepared to test the efficacy of the inventive device with a variety of pesticides (i.e., avermectin, azinphosmethyl, diazinon, and permethrin). Flies were allowed access to the samples and mortalities were high (90–100%) in all cases. These results demonstrate that a wide variety of pesticides can be incorporated into the coating.

Example 9

The Effectiveness on Different Species of Flies—Sample 21

To demonstrate the effectiveness of the spheres against different species of flies, Sample 21 was prepared with a yellow paint coating to simulate citrus and then tested against the Mediterranean fruit fly and the oriental fruit fly.

The samples were hung from branches of orange trees in an orange orchard located in Hawaii. Mediterranean fruit fly and Oriental fruit fly were used as test insects. The numbers of adult flies staying more than 1 minute on spheres were counted, and such flies were removed and kept in small cups for observation of mortality 24 hours later. Results appear in Table 8.

TABLE 8

| Insect | % Mortality |
|---|---|
| Mediterranean fruit fly | 86 |
| Oriental fruit fly | 96 |

Example 10

Safety of Handling

The safety of handling dimethoate-treated spheres was compared with the safety of handling apple foliage and fruit treated with a spray of dimethoate. Several apple trees (at the Horticultural Research Center, University of Massachusetts) received a spray of Digon 4E applied by mist-blower at the equivalent of 300 gal (approx. 1.14 m$^3$) water per acre (at label-recommended rate of 16 oz per 100 gal water). Spheres (Sample 16) were hung on adjacent apple trees at the same time and were not sprayed with Digon. Forty-eight hours and 30 days after application, sprayed foliage and fruits along with two spheres were brought to the laboratory for determination of surface dislodgeable residues of dimethoate. Surface dislodgeable residues from apples and spheres were removed by wiping the surface twice with a piece of cheese cloth. 20 mL portions of acetone were used to extract residues from the cheese cloth for 20 min. The surface dislodgeable residues from apple leaves were extracted using the method of Nigg et at. (1981). Samples were analyzed on a Varian 34000 GC equipped with a nitrogen/phosphorus detector. Results appear in Table 9.

TABLE 9

| Surface dislodgeable dimethoate residues (g/cm$^2$) | | |
|---|---|---|
| Sample | 48 hours | 30 days |
| Foliage | 1.04 | 1.1 |
| Fruit | 0.1 | 0.00 |
| Spheres | 0.20 | 0.15 |

These data demonstrate that there is much less residue on the surface of the spheres than on conventionally treated foliage.

What is claimed is:

1. A controlled release device for protecting fruit by attracting insects and delivering insecticide to insects over an extended period of time, comprising:
   (a) an outer layer having a thickness of 1 to 1,000 μm and comprising a porous water-insoluble polymeric material;
   (b) an inner layer in contact with the outer layer, the inner layer comprising 10 to 90 wt % of a water-soluble feeding stimulant capable of diffusing through said outer layer of (a) and attracting said insects in a carbohydrate which is at least partially gelatinized; and
   (c) an effective amount of a toxicant present on or in the outer layer, the inner layer, or both, wherein the shape and size of said device simulates a fruit to be protected.

2. The device of claim 1 wherein the porous water-insoluble polymeric material is paint, shellac, or linseed oil.

3. The device of claim 2 wherein the porous water-insoluble polymeric material is paint.

4. The device of claim 1 wherein the feeding stimulant is sucrose, glucose, fructose, molasses, maltodextrin or corn syrup.

5. The device of claim 1 wherein the feeding stimulant is a proteinaceous or lipid material.

6. The device of claim 5 wherein the feeding stimulant is corn flour or gluten.

7. The device of claim 1 wherein the carbohydrate is corn flour, cornstarch, wheat starch, or potato starch.

8. The device of claim 1 wherein the carbohydrate is partially gelatinized.

9. The device of claim 1 wherein the carbohydrate is fully gelatinized.

10. The device of claim 1 wherein the toxicant is present in the outer layer.

11. The device of claim 1 wherein the toxicant is present in the inner layer.

12. The device of claim 1 wherein the toxicant is present on the surface of the outer layer.

13. The device of claim 1 wherein the toxicant is dimethoate, phyloxine B, avermectin, azinphosmethyl, diazinon, permethrin, Imidacloprid, Malathion, or Methomyl.

14. The device of claim 1 further comprising a high boiling liquid in the inner layer.

15. The device of claim 14 wherein said high boiling liquid is glycerin.

16. The device of claim 1 further comprising a core in the center of the device in contact with the inner layer.

17. The device of claim 1 further comprising an insect attractant.

18. The device of claim 1 wherein said device is spherical.

19. A method of attracting pests and delivering pesticide to pests over an extended period of time by placing the controlled release device of claim 1 where pests are expected to be present.

20. The method of claim 19 wherein the porous water-insoluble polymeric material is paint, shellac, or linseed oil.

21. The method of claim 19 wherein the feeding stimulant is sucrose, glucose, fructose, molasses, maltodextrin or corn syrup.

22. The method of claim 19 wherein the carbohydrate is corn flour, cornstarch, wheat starch, or potato starch.

23. The method of claim 19 wherein the toxicant is dimethoate, phyloxine B, avermectin, azinphosmethyl, diazinon, permethrin, Imidacloprid, Malathion, or Methomyl.

24. The method of claim 19 further comprising a high boiling liquid in the inner layer.

25. The method of claim 24 wherein said high boiling liquid is glycerin.

* * * * *